(12) United States Patent
Weinberg

(10) Patent No.: US 10,888,225 B2
(45) Date of Patent: Jan. 12, 2021

(54) RED BLOOD CELLS AS VOLTAGE-SENSITIVE CONTRAST AGENTS

(71) Applicant: Weinberg Medical Physics, Inc., North Bethesda, MD (US)

(72) Inventor: Irving N. Weinberg, North Bethesda, MD (US)

(73) Assignee: WEINBERG MEDICAL PHYSICS INC, North Bethesda, MD (US)

( * ) Notice: Subject to any disclaimer, the term of this patent is extended or adjusted under 35 U.S.C. 154(b) by 147 days.

(21) Appl. No.: 16/185,191

(22) Filed: Nov. 9, 2018

(65) Prior Publication Data

US 2019/0142273 A1 May 16, 2019

Related U.S. Application Data

(60) Provisional application No. 62/584,459, filed on Nov. 10, 2017.

(51) Int. Cl.
| | |
|---|---|
| *A61B 5/00* | (2006.01) |
| *A61B 5/055* | (2006.01) |
| *G01R 33/54* | (2006.01) |
| *G01R 33/48* | (2006.01) |

(52) U.S. Cl.
CPC ............ *A61B 5/0042* (2013.01); *A61B 5/055* (2013.01); *G01R 33/4806* (2013.01); *G01R 33/54* (2013.01); *A61B 2576/026* (2013.01)

(58) Field of Classification Search
CPC ...... A61B 5/0042; A61B 5/055; G01R 33/54; G01R 33/4806
See application file for complete search history.

(56) References Cited

U.S. PATENT DOCUMENTS

| | | | | |
|---|---|---|---|---|
| 6,479,999 | B1 * | 11/2002 | DeMeester | G01R 33/4215 324/309 |
| 8,154,286 | B2 | 4/2012 | Weinberg | |
| 9,456,776 | B2 * | 10/2016 | Ando | A61B 5/4041 |
| 9,772,387 | B2 * | 9/2017 | Weinberg | G01R 33/4806 |
| 2002/0169373 | A1 * | 11/2002 | Kuth | G01R 33/4806 600/410 |
| 2004/0075434 | A1 * | 4/2004 | Vavrek | G01R 33/385 324/318 |
| 2005/0197561 | A1 * | 9/2005 | Elsinger | A61B 5/4082 600/410 |
| 2006/0122492 | A1 * | 6/2006 | Kucharczyk | A61B 5/0263 600/420 |
| 2006/0241382 | A1 * | 10/2006 | Li | A61B 5/055 600/410 |
| 2007/0167728 | A1 * | 7/2007 | Mistretta | G01R 33/561 600/410 |
| 2007/0247150 | A1 * | 10/2007 | van der Kouwe | G01R 33/4806 324/306 |
| 2009/0096451 | A1 * | 4/2009 | Aubert | G01R 33/4215 324/318 |
| 2009/0140737 | A1 * | 6/2009 | Aubert | G01R 33/385 324/309 |
| 2010/0194389 | A1 * | 8/2010 | Sutton | G01R 33/4806 324/309 |
| 2011/0068791 | A1 * | 3/2011 | Weinberg | G01R 33/3852 324/309 |
| 2011/0089947 | A1 * | 4/2011 | Weinberg | G01R 33/3852 324/309 |
| 2011/0306847 | A1 * | 12/2011 | Lowry | A61B 5/14542 600/301 |
| 2012/0184584 | A1 * | 7/2012 | Roses | A61K 31/4439 514/342 |
| 2013/0116540 | A1 * | 5/2013 | Li | G06T 7/0016 600/410 |
| 2013/0257428 | A1 * | 10/2013 | Weinberg | A61B 5/0042 324/309 |
| 2013/0267825 | A1 * | 10/2013 | Wohlgemuth | G01R 33/56341 600/410 |
| 2013/0271136 | A1 * | 10/2013 | Weinberg | A61B 5/055 324/309 |
| 2014/0066739 | A1 * | 3/2014 | He | A61B 5/048 600/377 |
| 2014/0336479 | A1 * | 11/2014 | Ando | A61B 5/14551 600/310 |
| 2014/0364721 | A1 * | 12/2014 | Lee | A61N 5/062 600/411 |
| 2015/0219732 | A1 * | 8/2015 | Diamond | A61B 5/0522 324/201 |
| 2016/0128592 | A1 * | 5/2016 | Rosen | A61B 5/04012 600/411 |
| 2016/0287100 | A1 * | 10/2016 | Tong | G01R 33/56545 |
| 2017/0049407 | A1 * | 2/2017 | Ando | A61B 5/055 |
| 2017/0128025 | A1 * | 5/2017 | Chen | A61B 5/7278 |
| 2017/0146625 | A1 * | 5/2017 | Beck | G01R 33/4835 |
| 2017/0164894 | A1 * | 6/2017 | Yoo | A61N 7/00 |
| 2017/0227617 | A1 | 8/2017 | Weinberg et al. | |
| 2017/0319565 | A1 * | 11/2017 | Roses | C07D 417/12 |
| 2017/0322273 | A1 * | 11/2017 | Truong | G01R 33/4806 |
| 2018/0035957 | A1 * | 2/2018 | Liu | F28D 1/035 |
| 2018/0256921 | A1 * | 9/2018 | Cho | A61N 5/1049 |

OTHER PUBLICATIONS https://blricrex.hypotheses.org/ressources/fmri; 2015.*
https://www.cell.com/neuron/pdf/50896-6273(16)30401-9.pdf; 2016.*
Shengbo Sang et al.: "Portable microsystem integrates multifunctional dielectrophoresis manipulations and a surface stress biosensor to detect red blood cells for hemolytic anemia"; Scientific Reports; Sep. 20, 2016; 8 pages.

* cited by examiner

*Primary Examiner* — Dixomara Vargas
(74) *Attorney, Agent, or Firm* — Barnes & Thornburg LLP

(57) ABSTRACT

An imaging apparatus and methodologies image a subject using Magnetic Resonance Imaging, wherein neuronal activity is assessed by measuring displacement of one or more red blood cells resulting from nearby electrical fields produced by the neuronal activity in the at least part of the subject's brain.

8 Claims, 1 Drawing Sheet

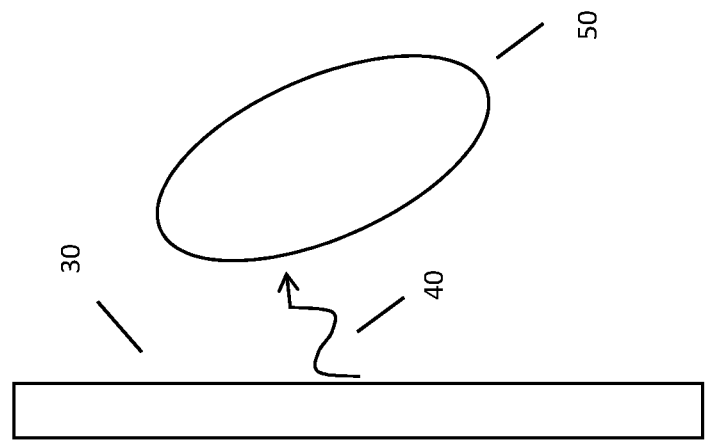
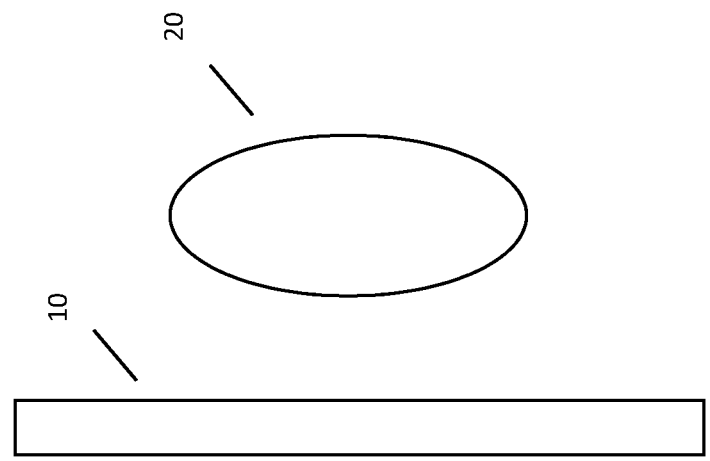

RED BLOOD CELLS AS VOLTAGE-SENSITIVE CONTRAST AGENTS

CROSS REFERENCE AND PRIORITY CLAIM

This patent application claims priority to U.S. Provisional Application Provisional Patent Application No. Patent Application Ser. No. 62/584,469, entitled "METHOD FOR IMPROVING SIGNAL-TO-NOISE RATIO IN MAGNETIC RESONANCE IMAGING," filed Nov. 10, 2017, the disclosure of which being incorporated herein by reference in its entirety.

FIELD

Disclosed embodiments provide a method and apparatus for Magnetic Resonance Imaging (MRI) for use in imaging, neuroscience, and/or neurology.

BACKGROUND

Researchers and clinicians have long sought the ability to noninvasively assess electrical activity in the brain. Conventionally known methods of collecting this information include magnetoencephalography and bold oxygenation level dependent magnetic resonance imaging ("BOLD MRI").

A BOLD MRI image is an image formed from magnetic resonance images, in which contrast is caused by the oxygenation state of blood, which is indirectly related to brain activity.

Conventional BOLD MRI equipment and methodologies are slow, with a time response of seconds, and feature poor spatial resolution (on the order of millimeters). Disclosed embodiments represent a different mechanism for creating images of electrical fields due to brain activity.

SUMMARY

The following presents a simplified summary in order to provide a basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to the more detailed description below.

Disclosed embodiments represent a different mechanism for creating images of electrical fields due to brain activity.

Disclosed embodiments image red blood cells in blood vessels within a brain of a subject with high spatial resolution to determine changes in positioning of those red blood cells that result from electric fields generated by firing neurons.

In accordance with at least some disclosed embodiments, a high resolution MRI may be used to measure size, angle, or position changes of one or more red blood cells resulting from the localized electric field(s) generated in a neuron or neurons as the neuron(s) is activated.

In accordance with at least some disclosed embodiments, blood cells in vessels within the brain are imaged with high spatial resolution, e.g., with a resolution that is more accurate than 30 microns.

In accordance with at least some disclosed embodiments, blood cells in vessels within the brain are imaged using high magnetic gradients (e.g., more than 100 mT/m).

In accordance with at least some disclosed embodiments, blood cells in vessels within the brain are imaged using rapid acquisitions (less than 100 milliseconds).

BRIEF DESCRIPTION OF THE FIGURES

The detailed description particularly refers to the accompanying FIGURES in which:

FIG. 1 is an illustration of the response of a red blood cell to the electric field from a neuron.

DETAILED DESCRIPTION

The description of specific embodiments is not intended to be limiting of the present invention. To the contrary, those skilled in the art should appreciate that there are numerous variations and equivalents that may be employed without departing from the scope of the present invention. Those equivalents and variations are intended to be encompassed by the present invention.

In the following description of various invention embodiments, reference is made to the accompanying drawings, which form a part hereof, and in which is shown, by way of illustration, various embodiments in which the invention may be practiced. It is to be understood that other embodiments may be utilized and structural and functional modifications may be made without departing from the scope and spirit of the present invention.

As explained above, in accordance with at least one disclosed embodiment, instrumentation and methodologies are provided that enable imaging red blood cells in blood vessels within a brain of a subject with high spatial resolution to determine changes in positioning of those red blood cells that result from electric fields generated by firing neurons.

Studies have shown that the position of red blood cells may be altered to some extent by application of electric field. For example, dielectropheresis can be used to selectively move live red blood cells as compared to dead blood cells, as taught in the Scientific Reports publication entitled "Portable microsystem integrates multifunctional dielectrophoresis manipulations and a surface stress biosensor to detect red blood cells for hemolytic anemia" (6:33626|DOI: 10.1038/srep33626publication; incorporated by reference in its entirety). Likewise, it is known that localized, electrical fields are generated within a subject's brain by action potentials of neurons or local potentials caused by one or more neurons within the subject's brain when those neurons are activated, or fire.

Disclosed embodiments image red blood cells in blood vessels within a brain of a subject with high spatial resolution to detect displacement of the position of one or more red blood cells for the purpose of determining when one or more neurons have been activated.

In vivo, blood cells within blood vessels in a subject's brain may be in motion due to vascular flow within the blood vessels. With high spatial resolution (e.g. 30 microns, which is similar to the size of a red-blood cell), displacement of the position of one or more flood cells resulting from electrical fields may be distinguished from the displacement of position due to the vascular flow. This is because displacement of red blood cell position resulting from the vascular flow may be in a straight line. To the contrary, displacement of red blood cell position resulting from localized electric fields may be angled or otherwise inconsistent with the straight line motion observed from vascular flow.

By imaging a subject's brain with high spatial resolution, disclosed embodiments image red blood cells in blood vessels to detect displacement of the position of one or more red blood cells for the purpose of determining when one or more nearby neurons have been activated.

As a result of the activation of one or more neurons, the blood cells in the brain blood vessels may be tilted or moved in a manner that is inconsistent with movement produced by vascular flow. In this way, the red blood cells within the subject's brain may be imaged to detect movement resulting from the localized electrical fields to determine when one or more nearby neurons are activated.

More specifically, the red blood cells may be repeatedly imaged rapidly and with high spatial resolution in order to detect the angular and/or linear displacement resulting from the application of the localized electrical fields produced by nearby neurons.

In accordance with at least one embodiment, additional images of the blood vessels of the brain may be collected to serve as, or provide, baselines in which the blood cells are not displaced by the local electrical fields. Such baseline image data may be collected when a subject is unconscious or performing calibration activities conventionally used as part of diagnostic tests performed to assess electrical activity in a subject's brain.

In this way, disclosed embodiments offer an innovative approach to noninvasively assessing electrical activity in subjects' brains. As a result, the disclosed embodiments provide the technical effect of adding additional and different data that may be used in such assessments beyond determining blood oxygenation state, which is indirectly related to brain activity.

Moreover, the disclosed embodiments provide the additional technical effect that assessments may be performed more quickly and with better spatial resolution than is conventionally possible.

It should be understood that an apparatus for applying magnetic fields for imaging of the red blood cells, blood vessels and brain of the subject may use electropermanent magnets, as taught by Irving Weinberg in US Pat. Pub. 20170227617, corresponding to U.S. patent application Ser. No. 15/427,426, entitled "METHOD AND APPARATUS FOR MANIPULATING ELECTROPERMANENT MAGNETS FOR MAGNETIC RESONANCE IMAGING AND IMAGE GUIDED THERAPY," incorporated herein by reference. Such electropermanent magnets may at one or more times create a magnetic field configuration for imaging of a subject's body part. It should be understood that the imaging capability may be through magnetic resonance imaging methods.

It should also be understood that one or more magnetic fields applied as part of imaging of the red blood cells, blood vessels and brain of the subject may be so rapidly applied so as not to cause unpleasant nerve stimulation, as taught by Irving Weinberg in issued U.S. Pat. No. 8,154,286, entitled "APPARATUS AND METHOD FOR DECREASING BIO-EFFECTS OF MAGNETIC FIELDS" (incorporated by reference) and patent applications related by priority claim, by Irving Weinberg, which are all incorporated herein by reference.

Thus, using this technology, in accordance with at least some disclosed embodiments, blood cells in vessels within the brain are imaged with high spatial resolution, e.g., with a resolution that is more accurate than 30 microns. Additionally, in accordance with at least some disclosed embodiments, red blood cells in vessels within the brain are imaged using high magnetic gradients (e.g., more than 100 mT/m, or 500 mT/m). In accordance with at least some disclosed embodiments, red blood cells in vessels within the brain are imaged using rapid acquisitions (less than 100 milliseconds) tp enable determination of displacement of position of one or more red blood cells.

Referring to FIG. 1, red blood cells 20 in vessels within the brain are imaged with high spatial resolution, e.g., with a resolution that is more accurate than 30 microns, using high magnetic gradients (e.g., more than 100 mT/m or more than 500 mT/m) and rapid acquisitions (less than 100 milliseconds). As the red blood cells move as a result of the localized electrical fields generated by action potentials of neurons or local potentials caused by one or more neurons 30, 10, the blood cells 50 are tilted or moved by the electric fields 40 from the neurons 30. Thus, imaging the red blood cells repeatedly (i.e., at least twice), rapidly and with high spatial resolution enables detection of the angular and/or linear displacement from the local electrical fields and, by association, nearby neuron activation.

In accordance with at least one embodiment, the high resolution MRI may be used to measure size or position changes in the neuron or neurons as the neurons are activated.

For the purposes of this specification, the term "subject" is understood to be a human or other animal with or without illness.

It is understood that an apparatus for analyzing the MRI image data described above in accordance with the disclosed methodology may be used in conjunction with other components, for example a computer and/or a power supply and/or coils for generating magnetic and/or electromagnetic fields, in order to attain a desired result of a meaningful image. It is understood that the image may use principles of proton magnetic resonance imaging, or magnetic resonance imaging of other particles (for example, electrons or sodium atoms) or other imaging principles (for example, magnetic particle imaging, or impedance imaging).

It should also be understood that the apparatus may be used to deliver therapy by manipulating magnetizable materials with the magnetic field produced by an MRI. It should be understood that such manipulation may be performed at one time, and that imaging may be performed at another time, in order to guide said manipulation.

For the purpose of the disclosed embodiments, the term "imaging" includes imaging technology that utilize components to form an image using magnetic resonance or magnetic particle imaging. It should be understood that such components include coils or magnets (or electro-permanent magnets) that polarize protons or other nuclei or electrons in one or more structures to be imaged, wherein gradient and/or radiofrequency coils acting upon atoms or molecules in a region of interest cause generation of electromagnetic waves that can be used to form an image using reconstruction techniques. The detection of the electromagnetic waves can be performed with a radiofrequency antenna or other detector sensitive to such electromagnetic radiation. Thus, although not shown in detail herein, it should be understood that the disclosed embodiments may be used in conjunction with a support structure that may hold an imaging system and may contain other components needed to operate or move the imaging system, for example, wheels and/or batteries.

Moreover, it should be understood that an associated display system is not shown but should be understood to be present in order to view images produced by the imaging system.

Further, it should be understood that disclosed embodiments may image one or more structures for segments of the one or more structure at a time, since it may be difficult in a single-sided MRI to obtain very good uniformity over the entirety of a structure to be imaged. It should be understood that the spatial resolution of certain portions of one or more structures to be imaged, e.g., breast tissues, may be different than in other portions, depending on the gradient applied at the time of image acquisition, which may be useful in order to better characterize certain regions of tissues.

It should be understood that the operations explained herein may be implemented in conjunction with, or under the control of, one or more general purpose computers running software algorithms to provide the presently disclosed functionality and turning those computers into specific purpose computers.

Moreover, those skilled in the art will recognize, upon consideration of the above teachings, that the above exemplary embodiments may be based upon use of one or more programmed processors programmed with a suitable computer program. However, the disclosed embodiments could be implemented using hardware component equivalents such as special purpose hardware and/or dedicated processors. Similarly, general purpose computers, microprocessor based computers, micro-controllers, optical computers, analog computers, dedicated processors, application specific circuits and/or dedicated hard wired logic may be used to construct alternative equivalent embodiments.

Moreover, it should be understood that control and cooperation of the above-described components may be provided using software instructions that may be stored in a tangible, non-transitory storage device such as a non-transitory computer readable storage device storing instructions which, when executed on one or more programmed processors, carry out the above-described method operations and resulting functionality. In this case, the term non-transitory is intended to preclude transmitted signals and propagating waves, but not storage devices that are erasable or dependent upon power sources to retain information.

Those skilled in the art will appreciate, upon consideration of the above teachings, that the program operations and processes and associated data used to implement certain of the embodiments described above can be implemented using disc storage as well as other forms of storage devices including, but not limited to non-transitory storage media (where non-transitory is intended only to preclude propagating signals and not signals which are transitory in that they are erased by removal of power or explicit acts of erasure) such as for example Read Only Memory (ROM) devices, Random Access Memory (RAM) devices, network memory devices, optical storage elements, magnetic storage elements, magneto-optical storage elements, flash memory, core memory and/or other equivalent volatile and non-volatile storage technologies without departing from certain embodiments. Such alternative storage devices should be considered equivalents.

While certain illustrative embodiments have been described, it is evident that many alternatives, modifications, permutations and variations will become apparent to those skilled in the art in light of the foregoing description. Accordingly, the various embodiments, as set forth above, are intended to be illustrative, not limiting. Various changes may be made without departing from the spirit and scope of the invention.

What is claimed:

1. An apparatus for magnetic resonance imaging of at least a part of a subject's brain to assess neuronal activity, the apparatus comprising:
    a magnetic resonance imaging system for performing an imaging process to image the at least part of the subject's brain, the magnetic resonance imaging system including at least one power source coupled to a processor that controls operation of the magnetic resonance imaging system to generate at least one magnetic field gradient for application to the at least part of the subject's brain to elicit an electromagnetic response from atoms and molecules included in the at least part of the subject's brain,
    wherein the magnetic resonance imaging system includes at least one detector that detects the electromagnetic response and the processor generates the image of the at least part of the subject's brain based on the detected electromagnetic response, wherein neuronal activity is assessed by measuring displacement of one or more red blood cells resulting from nearby electrical fields produced by the neuronal activity in the at least part of the subject's brain, and
    wherein the magnetic resonance imaging system images the at least part of the subject's brain with spatial resolution more accurate than 30 microns full-width at half-maximum.

2. The apparatus of claim 1, wherein the magnetic resonance imaging system images the at least part of the subject's brain with an image acquisition time of less than 100 milliseconds.

3. The apparatus of claim 1, wherein the magnetic resonance imaging system images the at least part of the subject's brain applies a magnetic gradient of more than 500 milliTeslas per meter.

4. The apparatus of claim 1, wherein the assessment of neuronal activity measures an increase in size of one or more neurons due to neuronal electrical activity.

5. A method for magnetic resonance imaging of at least a part of a subject's brain to assess neuronal activity, the method comprising:
    performing imaging processing using a magnetic resonance imaging system to image the at least part of the subject's brain, wherein the magnetic resonance imaging system includes at least one power source coupled to a processor that controls operation of the magnetic resonance imaging system to generate at least one magnetic field gradient for application to the at least part of the subject's brain to elicit an electromagnetic response from atoms and molecules included in the at least part of the subject's brain;
    detecting the electromagnetic response using at least one detector of the magnetic resonance imaging system;
    generating the image of the at least part of the subject's brain based on the detected electromagnetic response;
    assessing neuronal activity by measuring displacement of one or more red blood cells resulting from nearby electrical fields produced by the neuronal activity in the at least part of the subject's brain, and
    wherein the magnetic resonance imaging system generates the images of the at least a part of the subject's brain with spatial resolution more accurate than 30 microns full-width at half-maximum.

6. The method of claim 5, wherein the magnetic resonance imaging system generates the images of the at least a part of the subject's brain with an image acquisition time of less than 100 milliseconds.

7. The method of claim 5, wherein the magnetic resonance imaging system generates images of the at least a part of the subject's brain by applying a magnetic gradient of more than 500 milliTeslas per meter.

8. The method of claim 5, wherein the assessment of neuronal activity measures an increase in size of one or more neurons due to neuronal electrical activity.

\* \* \* \* \*